United States Patent [19]
De Sadeleer et al.

[11] Patent Number: 5,973,212
[45] Date of Patent: Oct. 26, 1999

[54] ERYTHRITOL COMPOSITIONS

[75] Inventors: Jos Willy Ghislain Corneel De Sadeleer, Holsbeek; Michel Henri AndréGonze, Brussels, both of Belgium

[73] Assignee: Cerestar Holding B.V., Sas Van Gent, Netherlands

[21] Appl. No.: 09/042,729

[22] Filed: Mar. 17, 1998

Related U.S. Application Data

[63] Continuation of application No. 08/015,089, Feb. 9, 1993, abandoned, which is a continuation of application No. 07/813,091, Dec. 24, 1991, abandoned.

[30] Foreign Application Priority Data

Jan. 2, 1991 [GB] United Kingdom .................... 9100009

[51] Int. Cl.$^6$ .................................................. C07C 31/18
[52] U.S. Cl. ........................... 568/852; 568/868; 426/548
[58] Field of Search .................................. 568/852, 868; 426/548

[56] References Cited

U.S. PATENT DOCUMENTS

| | | |
|---|---|---|
| 3,639,169 | 2/1972 | Broeg . |
| 4,886,677 | 12/1989 | Kondou . |
| 4,902,525 | 2/1990 | Kondou . |
| 5,013,557 | 5/1991 | Tai . |
| 5,080,916 | 1/1992 | Kondou ...................................... 426/96 |

FOREIGN PATENT DOCUMENTS

| | | |
|---|---|---|
| 0287957 | 10/1988 | European Pat. Off. . |
| 0304915 | 3/1989 | European Pat. Off. . |
| 0325790 | 8/1989 | European Pat. Off. . |
| 0430663 | 5/1991 | European Pat. Off. . |
| 252003 | 8/1986 | Germany . |
| 1613180 | 1/1988 | Russian Federation . |

OTHER PUBLICATIONS

Sigma, Biochemicals, Organic Compounds for Research and Diagnostic Reagents, 1990, p. 449.
Remington's Pharmaceutical Sciences, pp. 1234, 1260, 1578, 1975.

*Primary Examiner*—Rebecca Cook
*Attorney, Agent, or Firm*—Pillsbury Madison & Sutro LLP

[57] ABSTRACT

The invention comprises spray dried erythritol which may also be agglomerated. The product is a free-flowing powder which preferably has 60% or more of its particles in the range 10 to 250 microns. The product is useful as a sweetener for which it is particularly adapted to be combined with a synthetic sweetener such as aspartame. The product is also useful in combination with a binder, particularly a potato maltodextrin, as a tabletting composition. The invention also comprises a process for making the product.

5 Claims, No Drawings

ERYTHRITOL COMPOSITIONS

This is a continuation of application Ser. No. 08/015,089, filed Feb. 9, 1993 abandoned which is a FWC of application Ser. No. 07/813,091, filed Dec. 24, 1991 abandoned.

The present invention relates to erythritol, in particular to a form of erythritol useful in sweetening applications.

Erythritol is a tetra-hydroxy sugar alcohol which may be produced commercially by fermentation processes. It has aroused considerable interest recently because it has a sweet taste and is at the same time both non-caloric and non-cariogenic i.e. it has an ideal combination of properties for use as a sweetener in dietetic and pharmaceutical compositions.

The patent literature issuing in the last five years has reflected the potential value of erythritol as a sweetener and it has been described for use both generally and in specific applications in the following publications.

European patent application 9325 describes in general the use of erythritol as a non-cariogenic sugar replacement.

European patent application 287095 describes the surface treatment of dehydrated foods and Japanese patent application 209363/87 the surface treatment of other foodstuffs with erythritol.

European patent application 303295 describes the use of erythritol in hard candy.

European patent application 301502 describes the use of erythritol as sweetener in fermented milk products.

Japanese patent application 91598/87 describes erythritol as sweetener for a beverage powder.

Japanese patent application 207798/88 describes a process for making a chewing gum containing erythritol.

Japanese patent applications 334818/87 and 51651/88 describe the use of erythritol as an icing agent and in fondant manufacture.

Japanese patent application 255828/88 describes chocolate containing erythritol.

Japanese patent application 144747/88 describes a baking dough which contains erythritol.

Japanese patent application 94510/88 describes erythritol as a sweetener for ice-cream.

Erythritol has about 60% the sweetness of sucrose and it has therefore been proposed to use combinations of erythritol with minor amounts of intense sweeteners. Thus, European patent application 9325 describes a combination of erythritol and saccharin, European patent application 287957 the use of erythritol with aspartame, glycerrhizin, stevioside and thaumatin and Japanese patent application 140519/87 the use of erythritol together with aspartame.

When erythritol is used with an intense sweetener such as aspartame as a "table top" sweetener i.e. as a replacement for sucrose in quantity of erythritol and intense sweetener should have a level of sweetness equivalent to a similar quantity of sucrose. Such table-top sweeteners based on erythritol are described in European patent applications 304915 and 325790.

Erythritol is a highly crystalline solid and use is made of this crystallinity in several of the applications described above. One problem when making a blend of erythritol and intense sweetener however is to ensure that the intense sweetener, which is present only in very small quantity, is evenly distributed throughout the mass of the erythritol. The present invention provides a means of ensuring an even level of sweetness in an erythritol/intense sweetener table top composition and also provides a form of erythritol which is useful in specialised applications such as tabletting, chewing gum, chocolate, crystallised tablets and fondants.

Accordingly, the invention comprises spray dried erythritol and spray dried erythritol which has also been agglomerated. By spray drying erythritol from a solution of erythritol and an intense sweetener a composition may be obtained in which the intense sweetener is evenly distributed throughout the erythritol at any desired level of incorporation. Spray dried erythritol although still crystalline is a light, free flowing powder which may, by including an agglomeration step in the preparative process, be obtained in a range of particle sizes depending upon the application required. For many purposes, it is preferred that the quantity of particles of size less than 10 microns is less than 20% by weight. It is also advantageous for the quantity of particles of size greater than 250 microns to be less than 20% by weight. Such a product suitably has a specific surface in the range of 0.01 to 0.30 $m^2/g$, preferably 0.04 to 0.20 $m^2/g$. The product according to the invention can readily be made in high yield with a particle size in the range 10 to 250 microns. By contrast, if a product having the same particle size is made by milling and sieving erythritol crystals, a large amount of dust is produced owing to the fragility of the erythritol crystal.

The erythritol may be spray-dried in conventional spray drying equipment in which an aqueous solution of erythritol, optionally together with additives such as an intense sweetener, is atomised to form a spray of droplets which are contacted with hot gases to produce a dispersed dry product. The aqueous solution may contain 15 to 80% preferably 30 to 60% by weight erythritol, more preferably 40 to 50% by weight. The temperature of the aqueous erythritol solution fed to the atomiser is suitably 30 to 90° C., preferably 35 to 70° C. and the temperature of the hot gas, usually air, used in the drying is preferably 100 to 250° C. The temperature of the material leaving the drier is suitably held below 120° C. eg. about 100° C.

If desired, the spray dried erythritol may be agglomerated to produce a product with a more controlled particle size and particle size distribution. The agglomeration step may be integrated with the spray-drying process or may take place separately. The step may be carried out by spraying erythritol powder with a binding agent, most usually water, while keeping the particles in a state of gentle agitation. The agitation leads to the growth of the particles by random coalescence and by crushing and layering. Once the particles have reached the desired size the moisture is evaporated by hot air. In the integrated process the particles may be agitated in a fluidised bed and unwanted fine particles recycled to the spray drying tower.

The product according to the invention finds application in table top compositions and in other applications where it is desired to use mixtures of constant composition comprising erythritol and an intense, or other sweetener. It is also useful in tabletting compositions and in applications such as chewing gum and chocolate manufacture where a readily dispersible form of erythritol is required. When dissolved in an aqueous liquid erythritol is known to have a cooling effect because of its negative heat of solution. We have found that the perception of this cooling effect by the mouth is dependant upon the particle size of the erythritol crystals and for maximum effect it is desirable to use small but integral and non-fragmented crystals in fondants, icing agents, chewing gum etc. As the product of the invention may readily be provided as small, relatively perfect crystals it is a particularly useful form of erythritol for use in such applications.

When the product of the invention is to be used in the production of tablets it is preferred that the erythritol should be spray dried in the form of a composition with a suitable binding agent. We have found that maltodextrins are useful as binding agents particularly potato maltodextrins and especially low DE potato maltodextrins ie of DE 1 to 5, particularly 2 to 3. The solid component of the composition to be spray-dried may comprise 1 to 50% by weight binding agent and 99 to 50% by weight erythritol, preferably 2 to 20% by weight binding agent and 98 to 80% by weight erythritol, particularly 3 to 10% by weight binding agent and 97 to 90% by weight erythritol.

The invention will now be further described with reference to the following Examples in which a pilot scale spray tower was used, the aqueous erythritol solution being fed to the tower at a temperature between 38° and 85° C. where it met a flow of hot air and was subjected to a turbulent action which had the effect of agglomerating as well as drying the erythritol.

EXAMPLE 1

| | | |
|---|---|---|
| Erythritol dry substance | 28% | |
| Solution inlet temperature | 38° C. | |
| Air inlet temperature | 200° C. | |
| Air outlet temperature | 95° C. | |
| Particle size distribution | >250 | 15% |
| of the product (microns) | 250–150 | 22% |
| | 150–70 | 26% |
| | 70–10 | 30% |
| | <10 | 7% |
| Specific surface | 0.048 m$^2$/g | |

EXAMPLE 2

| | | |
|---|---|---|
| Erythritol dry substance | 28% | |
| Solution inlet temperature | 38° C. | |
| Air inlet temperature | 160° C. | |
| Air outlet temperature | 102° C. | |
| Particle size distribution | >250 | 10% |
| of the product (microns) | 250–150 | 21% |
| | 150–70 | 26% |
| | 70–10 | 34% |
| | <10 | 9% |
| Specific surface | 0.090 m$^2$/g | |

EXAMPLE 3

| | | |
|---|---|---|
| Erythritol dry substance | 45% | |
| Solution inlet temperature | 38° C. | |
| Air inlet temperature | 133° C. | |
| Air outlet temperature | 100° C. | |
| Particle size distribution | >250 | 9% |
| of the product (microns) | 250–150 | 19% |
| | 150–70 | 25% |
| | 70–10 | 37% |
| | <10 | 10% |
| Specific surface | 0.094 m$^2$/g | |

EXAMPLE 4

| | | |
|---|---|---|
| Erythritol dry substance | 45% | |
| Solution inlet temperature | 38° C. | |
| Air inlet temperature | 122° C. | |
| Air outlet temperature | 96° C. | |
| Particle size distribution | >250 | 5% |
| of the product (microns) | 250–150 | 12% |
| | 150–70 | 24% |
| | 70–20 | 34% |
| | 20–10 | 13% |
| | <10 | 12% |
| Specific surface | 0.12 m$^2$/g | |

EXAMPLE 5

| | | |
|---|---|---|
| Erythritol dry substance | 60% | |
| Solution inlet temperature | 55° C. | |
| Air inlet temperature | 120° C. | |
| Air outlet temperature | 100° C. | |
| Particle size distribution | >250 | 4% |
| of the product (microns) | 250–150 | 1% |
| | 150–70 | 2% |
| | 70–20 | 37% |
| | 20–10 | 32% |
| | <10 | 24% |
| Specific surface | 0.17 m$^2$/g | |

EXAMPLE 6

| | | |
|---|---|---|
| Erythritol dry substance | 60% | |
| Solution inlet temperature | 55° C. | |
| Air inlet temperature | 120° C. | |
| Air outlet temperature | 100° C. | |
| Particle size distribution | >250 | 6% |
| of the product (microns) | 250–150 | 1% |
| | 150–70 | 3% |
| | 70–20 | 37% |
| | 20–10 | 30% |
| | <10 | 23% |
| Specific surface | 0.14 m$^2$/g | |

EXAMPLE 7

| | | |
|---|---|---|
| Erythritol dry substance | 30% | |
| Solution inlet temperature | 50° C. | |
| Air inlet temperature | 115° C. | |
| Air outlet temperature | 80° C. | |
| Particle size distribution | >250 | 4% |
| of the product (microns) | 250–150 | 10% |
| | 150–70 | 28% |
| | 70–20 | 36% |
| | 20–10 | 11% |
| | <10 | 11% |
| Specific surface | 0.11 m$^2$/g | |

EXAMPLE 8

| | | |
|---|---|---|
| Erythritol dry substance | 50% | |
| Solution inlet temperature | 85° C. | |
| Air inlet temperature | 126° C. | |
| Air outlet temperature | 98° C. | |
| Particle size distribution | >250 | 10% |
| of the product (microns) | 250–150 | 17% |
| | 150–70 | 26% |
| | 70–20 | 28% |
| | 20–10 | 10% |
| | <10 | 9% |
| Specific surface | 0.12 m$^2$/g | |

EXAMPLE 9

In this Example a form of spray-dried erythritol was prepared which was specially adapted for use in tabletting.

The spray drying tower which was used was a Niro Atomiser FSD Pilot Plant Unit of height 2740 mm and top diameter 1200 mm. The unit was provided with a two fluid nozzle, a cyclone system for separating fines from the exit gas and a fluid bed drying system adapted to receive product leaving the tower. The solution which was fed to the tower comprised an aqueous solution containing 45% by weight dissolved solids which consisted in turn of 95% by weight erythritol

| | | |
|---|---|---|
| Erythritol dry substance | 60° C. | |
| Air inlet temperature | 180° C. | |
| Air pressure to the nozzle | 3 bar | |
| Air flow through the nozzle | 215 Kg/hr | |
| Air outlet temperature | 95° C. | |
| Fluid bed temperature | 95° C. | |
| Air flow to fluidised bed | 140 Kg/hr | |
| Particle size distribution | >400 | 2.7% by weight |
| of the product | 250–400 | 5.3% |
| | 200–250 | 5.3% |
| | 125–200 | 14.9% |
| | 100–125 | 8.6% |
| | 80–100 | 10.9% |
| | 63–80 | 31.5% |
| | <63 | 20.8% |

The action of the air flow in the tower and the fluidised bed had the effect of agglomerating as well as spray drying the product.

The product of the spray drying process was mixed with 1.5% by weight magnesium stearate and formed into a tablet in a Fette P1000 tabletting machine. The tablet was formed under a compression force of 15 Kg and was 18 mm in diameter with a thickness of 6 mm.

The tablet was evaluated in a Fette "Checkmaster 3" which measured the tablet weight, thickness and hardness (compression to break). The hardness value of the tablet described above was 3.2 Kg. An attempt to produce a tablet without the maltodextrin binder was unsuccessful, the tablet being too soft to be of use.

What is claimed is:

1. A light, free-flowing powder comprising at least 80% erythritol obtained by spray drying an aqueous erythritol solution and a maltodextrin binder.

2. A light, free-flowing powder according to claim 1, wherein the maltodextrin is a potato maltodextrin of DE 1 to 5.

3. A light, free-flowing powder according to claim 1, wherein which also comprises an intense sweetener.

4. A light, free flowing powder according to claim 3, wherein the intense sweetener is aspartame.

5. A tablet obtained by forming a table from light, free-flowing powder according to claim 1.

* * * * *